(12) United States Patent
Hoshi

(10) Patent No.: US 6,180,564 B1
(45) Date of Patent: Jan. 30, 2001

(54) HERBICIDAL COMPOSITION

(75) Inventor: Hisayuki Hoshi, Toyonaka (JP)

(73) Assignee: Sumitomo Chemical Company, Limited (JP)

(*) Notice: Under 35 U.S.C. 154(b), the term of this patent shall be extended for 0 days.

(21) Appl. No.: 09/357,967

(22) Filed: Jul. 21, 1999

(30) Foreign Application Priority Data

Jul. 23, 1998 (JP) .................................... 10-207712

(51) Int. Cl.$^7$ .................................................. A01N 43/72
(52) U.S. Cl. ............................................................. 504/132
(58) Field of Search ..................................... 504/116, 132

(56) References Cited

U.S. PATENT DOCUMENTS

| | | | |
|---|---|---|---|
| 5,045,105 | 9/1991 | Grossmann et al. | 71/74 |
| 5,062,884 | 11/1991 | Plath et al. | 71/95 |

FOREIGN PATENT DOCUMENTS

19633271 * 2/1998 (DE) .

OTHER PUBLICATIONS

The Agrochemicals Handbook, 3rd Ed., A0034, 1991.*

* cited by examiner

*Primary Examiner*—Jose' G. Dees
*Assistant Examiner*—Alton Pryor
(74) *Attorney, Agent, or Firm*—Birch, Stewart, Kolasch & Birch LLP

(57) ABSTRACT

The present invention provides for herbicidal composition comprising (i) 3-isopropyl-1H-2,1,3-benzothiadiazin-4 (3H)-one 2,2-dioxide, and (ii) ethyl 2-chloro-3-[2-chloro-5-(1,3-dioxo-4,5,6,7-tetrahydroisoindolin-2-yl)phenyl] acrylate as active ingredients. The present inventive composition can control a wide variety of weeds in corn fields, soybean fields, wheat fields, barley fields, oats fields, rye fields, rice fields, paddy fields or the like, with selectivity to crops. Methods for controlling weeds are also provided.

13 Claims, No Drawings

HERBICIDAL COMPOSITION

FIELD OF THE INVENTION

The present invention relates to a herbicidal composition.

BACKGROUND OF THE INVENTION

Currently, various herbicides are being utilized, but since there are various weeds that are targets of control, and because the growth of weeds continues for a long time, a herbicide is desired that has a higher herbicidal activity, a faster appearance of herbicidal effect, a wider herbicidal spectrum and that is safe for crops.

SUMMARY OF THE INVENTION

The present inventor has intensely studied to seek out an excellent herbicide, and has found that by applying a herbicidal composition (hereinafter, referred to as the present inventive composition) which comprises, as active ingredients, (i) 3-isopropyl-1H-2,1,3-benzothiadiazin-4 (3H)-one 2,2-dioxide (common name: bentazone, hereinafter, referred to as bentazone), and (ii) ethyl 2-chloro-3-[2-chloro-5-(1,3-dioxo-4,5,6,7-tetrahydroisoindolin-2-yl) phenyl]acrylate (common name: cinidon-ethyl, hereinafter, referred to as cinidon-ethyl), various weeds that emerge or grow in crop-lands or non-crop-lands can be controlled effectively, thereby completing the present invention. That is, since the herbicidal effect of the present inventive composition is synergistically increased as compared with the cases where the active ingredients are independently used, the amount used thereof can be reduced. By using the present inventive composition, the time necessary for appearance of a herbicidal effect can be shortened, and a broadened weed control spectrum can be achieved synergistically, as compared with the cases where the active ingredients are independently used. Moreover, a wide variety of weeds can be controlled selectively, without producing problems of phytotoxicity against crops such as corn, soybean, wheat, barley, oats, rye and rice. In particular, when used in a corn field or soybean field, the present composition is excellent for selectivity. Accordingly, the present invention has been obtained.

DETAILED DESCRIPTION OF THE INVENTION

The present invention provides a herbicidal composition that comprises, as active ingredients, (i) bentazone and (ii) cinidon-ethyl.

Bentazone is a compound described in Farm Chemicals Handbook, 1995 (established by Meister Publishing Co., 1995) page C48 and the like.

Cinidon-ethyl is a compound described in JP 62-185071 A.

The present inventive herbicidal compositions are excellent as herbicides because they have a herbicidal activity against a wide variety of weeds with good selectivity between weeds and crops, and they exhibit an excellent herbicidal activity in no-till cultivation and non-agricultural fields as well as in till cultivation.

The present inventive herbicidal compositions have a herbicidal activity against the following variations of weeds that cause problems for crops in fields of corn, soybean, wheat, barley, oats, rye or rice.

Polygonaceous weeds:
wild buckwheat (*Polygonum convolvulus*), pale smartweed (*Polygonum lapathifolium*), pennsylvania smartweed (*Polygonum pensylvanicum*), ladysthumb (*Polygonum persicaria*), curly dock (*Rumex crispus*), broad leaf dock (*Rumex obtusifolius*) and Japanese knotweed (*Polygonum cuspidatum*);

Portulacaceous weeds:
common purslane (*Portulaca oleracea*);

Caryophyllaceous weeds:
common chickweed (*Stellaria media*);

Chenopodiaceous weeds:
common lambsquarters (*Chenopodium album*) and kochia (*Kochia scoparia*)

Amaranthaceous weeds:
redroot pigweed (*Amaranthus retroflexus*) and smooth pigweed (*Amaranthus hybridus*);

Cruciferous (brassicaceous) weeds:
wild radish (*Raphanus raphabistrum*), wild mustard (*Sinapis arvensis*) and Shepherds purse (*Capsella bursa-pastoris*);

Leguminous (fabaceous) weeds:
hemp sesbania (*Sesbania exaltata*), sicklepod (*Cassia obtusifolia*), Florida beggarweed (*Desmodium tortuosum*), and white clover (*Trifolium repens*);

Malvaceous weeds:
velvetleaf (*Abutilon theophrasti*) and prickly sida (*Sida spinosa*);

Violaceous weeds:
field pansy (*Viola arvensis*) and wild pansy (*Viola tricolor*);

Rubiaceous weeds:
catchweed bedstraw (*Galium aparine*);

Convolvulaceous weeds:
ivyleaf morningglory (*Ipomoea hederacea*), tall morningglory (*Ipomoea purpurea*), entireleaf morningglory (*Ipomoea hederacea* var. *integriuscula*), pitted morningglory (*Ipomoea lacunosa*) and field bindweed (*Convolvulus arvensis*);

Labiate weeds:
red deadnettle (*Lamium purpureum*) and henbit (*Lamium amplexicaure*);

Solanaceous weeds:
jimsonweed (*Datura stramonium*) and black nightshade (*Solanum nigrum*);

Scrophulariaceous weeds:
Persian speedwell (*Veronica persica*) and Ivyleaf speedwell (*Veronica hederifolia*);

Composite weeds:
common cocklebur (*Xanthium pensylvanicum*), common sunflower (*Helianthus annuus*), scentless chamomile (*Matricaria perforata* or *inodora*), corn marigold (*Chrysanthemum segetum*), pineappleweed (*Matricaria matricarioides*), common ragweed (*Ambrosia artemisiifolia*), giant ragweed (*Ambrosia trifida*), Mare'stail (*Erigeron canadensis*), *Artemisia princeps, Solidago altissima;*

Boraginaceous weeds:
forget-me-not (*Myosotis arvensis*)

Asclepiadaceous weeds:
common milkweed (*Asclepias syriaca*)

Euphorbiaceous weeds:
sun spurge (*Euphorbia helioscopia*) and spotted spurge (*Euphorbia maculata*)

Graminaceous weeds:
barnyardgrass (*Echinochloa crus-galli*), green foxtail (*Setaria viridis*), giant foxtail (*Setaria faberi*), large crabgrass (*Digitaria sanguinalis*), goosegrass (*Eleusine indica*), annual bluegrass (*Poa annua*), blackgrass (*Alopecurus myosuroides*), wild oat (*Avena fatua*), johnsongrass (*Sorghum halepense*), quackgrass (*Agropyron repens*), downy brome (*Bromus tectorum*), Bermudagrass (*Cynodon dactylon*), fall panicum (*Panicum dichotomiflorum*), *Panicum texanum* and shattercane (*Sorghum vulgare*);

Commelinaceous weeds:
common dayflower (*Commelina communis*)
Equisetaceous weeds:
field horsetail (*Equisetum arvense*);
Cyperaceous weeds:
rice flatsedge (*Cyperus iria*), purple nutsedge (*Cyperus rotundus*) and yellow nutsedge (*Cyperus esculentus*)

At the same time the present inventive composition exhibits no significant phytotoxicity on crops such as corn, soybean, wheat, barley, oats, rye and rice. In particular, when used in corn field or soybean field, the present composition is excellent for selectivity.

When the present inventive composition is used in paddy fields, it may be sprayed to foliage of weeds in a preplant burndown application before flooding, or after seeding rice it may be sprayed to foliage of weeds in a delayed pre-emergence application before flooding, preferably.

The present composition effectively exhibits an excellent herbicidal activity on weeds, e.g., dicotyledonous plants such as hemp sesbania (*Sesbania exaltata*), ivyleaf morningglory (*Ipomoea hederacea*), tall morningglory (*Pharbitis purpurea*), entireleaf morningglory (*Ipomoea hederacea* var. *integriuscula*), pitted morningglory (*Ipomoea lacunosa* L.), common cocklebur (*Xanthium pensylvanicum*), and pensylvania smartweed (*Polygonum pensylvanicum*); and monocotyledonous plants such as barnyardgrass (*Echinochloa crus-galli*), southern crabgrass (*Digitaria ciliaris*), goosegrass (*Eleusine indica*), sprangletop (*Leptochloa chinensis*), broadleaf signalgrass (*Brachiaria platyphylla*), umbrella sedge (*Cyperus difformis*), and rice flatsedge (*cyperus iria*), while it exhibits no significant phytotoxicity on rice.

For the present inventive composition, the mixing ratio of bentazone to cinidon-ethyl for active ingredients, may vary with the species of weeds to be controlled, the situation, conditions of application and the like, but is usually in the range from about 4:1 to 400:1 by weight, preferably, in the range of about 4:1 to 40:1 by weight.

The present inventive composition is usually utilized after formulating into emulsifiable concentrates, wettable powders, flowables, granules or the like by mixing a solid carrier(s), liquid carrier(s), or the like, and when necessary, adding surfactant(s) or other adjuvants for formulation. The formulations thereof generally comprise bentazone and cinidon-ethyl in a total amount of about 0.5 to 90% by weight, and preferably about 1 to 80% by weight.

In an event of formulation, as the utilized solid carrier or diluent, examples include fine powders or granules of clays (e.g., kaolinite, diatomaceous earth, synthetic hydrated silicon oxide, Fubasami clay, bentonite, acid clay), talc and other inorganic minerals (e.g., sericite, powdered quartz, powdered sulfur, activated carbon, calcium carbonate), and chemical fertilizers (e.g., ammonium sulfate, ammonium phosphate, ammonium nitrate, ammonium chloride, urea); and as the liquid carrier or diluent, examples include water, alcohols (e.g., methanol, ethanol), ketones (e.g., acetone, methyl ethyl ketone, cyclohexanone), aromatic hydrocarbons (e.g., toluene, xylene, ethylbenzene, methylnaphthalene), non-aromatic hydrocarbons (e.g., hexane, cyclohexane, kerosine), esters (e.g., ethyl acetate, butyl acetate), nitriles (e.g., acetonitrile, isobutyronitrile), ethers (e.g., dioxane, diisopropyl ether), acid amides (e.g., dimethylformamide, dimethylacetamide), and halogenated hydrocarbons (e.g., dichloroethane, trichloroethylene).

As the surfactant, examples include alkylsulfic esters, alkylsulfonic salts, alkylarylsulfonic salts, alkyl aryl ethers and their polyoxyethylene derivatives, polyethylene glycol ethers, polyhydric alcohol esters and sugar alcohol derivatives.

As the other adjuvants for formulation, examples include adhesive agents or dispersing agents, such as casein, gelatin, polysaccharides (e.g., starch, gum arabic, cellulose derivatives, alginic acid), lignin derivatives, bentonite, and synthetic water-soluble polymers (e.g., polyvinyl alcohol, polyvinyl pyrrolidone, polyacrylic acid); and stabilizers such as PAP (isopropyl acid phosphate), BHT (2,6-tert-butyl-4-methylphenol), BHA (2-/3-tert-butyl-4-methoxyphenol), vegetable oils, mineral oils, fatty acids, and fatty acid esters.

The present inventive composition can also be prepared by formulating each of the active ingredients by a formulation methods as described above, and then mixing these formulations together.

The present inventive composition formulated in the above manner may be applied to plants by itself (i.e., as it is) or with a dissolving thereof in water. The present composition may further be utilized by mixing with other herbicide(s) to provide an enhancement in herbicidal activity, and further they may be utilized in combination with insecticides, bactericides, fungicides, plant growth regulators, fertilizers, safeners or soil conditioners.

The application amount of the present inventive composition may vary with the mixing rate of bentazone to cinidon-ethyl, weather conditions, formulation, application timing, application method, application location, objective weed to be controlled or objective crop to be protected, but the total amount of the active ingredient compounds applied per 1 hectare is usually from about 50 to 5,000 g, and preferably 200 to 2,000 g. Emulsifiable concentrates, wettable powders, flowables or the like are applied after diluting the predetermined amount per 1 hectare with about 100 to 1000 L of water.

Hereinafter, the formulation examples are given. Parts represents parts by weight in the examples below.

FORMULATION EXAMPLE 1

Five parts of cinidon-ethyl, 25 parts of bentazone, 3 parts of calcium ligninsulfonate, 2 parts of sodium laurylsulfate and 65 parts of synthetic hydrated silicon oxide are well pulverized and mixed to obtain a wettable powder.

FORMULATION EXAMPLE 2

0.4 Part of cinidon-ethyl, 40 parts of bentazone, 3 parts of calcium ligninsulfonate, 2 parts of sodium laurylsulfate and 54.6 parts of synthetic hydrated silicon oxide are well pulverized and mixed to obtain a wettable powder.

FORMULATION EXAMPLE 3

0.5 Part of cinidon-ethyl, 25 parts of bentazone, 3 parts of calcium ligninsulfonate, 2 parts of sodium laurylsulfate and 69.5 parts of synthetic hydrated silicon oxide are well pulverized and mixed to obtain a wettable powder.

FORMULATION EXAMPLE 4

0.5 Part of cinidon-ethyl, 10 parts of bentazone, 3 parts of calcium ligninsulfonate, 2 parts of sodium laurylsulfate and 84.5 parts of synthetic hydrated silicon oxide are well pulverized and mixed to obtain a wettable powder.

FORMULATION EXAMPLE 5

Five parts of cinidon-ethyl, 25 parts of bentazone, 3 parts of polyoxyethylene sorbitan monooleate, 3 parts of CMC (carboxymethyl cellulose) and 64 parts of water are mixed and wet pulverized until the particle size thereof is 5 microns or smaller, to thereby obtain a flowable.

FORMULATION EXAMPLE 6

0.4 Part of cinidon-ethyl, 40 parts of bentazone, 3 parts of polyoxyethylene sorbitan monooleate, 3 parts of CMC (carboxymethyl cellulose) and 53.6 parts of water are mixed and wet pulverized until the particle size thereof is 5 microns or smaller, to thereby obtain a flowable.

FORMULATION EXAMPLE 7

0.5 Part of cinidon-ethyl, 25 parts of bentazone, 3 parts of polyoxyethylene sorbitan monooleate, 3 parts of CMC (carboxymethyl cellulose) and 68.5 parts of water are mixed and wet pulverized until the particle size thereof is 5 microns or smaller, to thereby obtain a flowable.

FORMULATION EXAMPLE 8

0.5 Part of cinidon-ethyl, 10 parts of bentazone, 3 parts of polyoxyethylene sorbitan monooleate, 3 parts of CMC (carboxymethyl cellulose) and 83.5 parts of water are mixed and wet pulverized until the particle size thereof is 5 microns or smaller, to thereby obtain a flowable.

Hereinafter, the test examples are given. Evaluation Criteria The herbicidal activity is evaluated at 11 levels with indices of 0 to 10, i.e., shown by numeral "0", "1", "2", "3", "4", "5", "6", "7", "8", "9", or "10", wherein "0" means that there was no or little difference in the degree of germination or growth between the treated plants and the untreated plants at the time of evaluation, and "10" means that the test plants died completely or their germination or growth was completely inhibited.

TEST EXAMPLE 1

Plastic pots each having an area of 25.5×17.3 cm$^2$ and a depth of 7 cm were filled with upland soil, then seeded with corn (*Zea mays*), soybean (*Glycine max*), common lambsquarters (*Chenopodium album*), common ragweed (*Ambrosia artemisiifolia*) and pale smartweed (*Polygonum lapathifolium*). Then, in a greenhouse, corn was grown for 20 days; soybean and pale smartweed were grown for 25 days; and common lambsquarters and common ragweed were grown for 30 days.

A cinidon-ethyl emulsifiable concentrate obtained by mixing well together 10 parts of cinidon-ethyl, 14 parts of polyoxyethylene styrylphenyl ether, 6 parts of calcium dodecylbenzenesulfonate, 35 parts of xylene and 35 parts of cyclohexanone, a formulated bentazone product (trade name: Basagran; manufacturer, BASF AG) and a mixture of said cinidon-ethyl emulsifiable concentrate and said formulated bentazone product were independently diluted in their prescribed amounts with water, and then uniformly sprayed over the test plants with a small sprayer. After the application, the test plants were grown in the greenhouse for 20 days, and the herbicidal activity was then examined. The results are given in Table 1. The marks in the table are defined as follows.

T: Corn, D: Soybean, S: Common lambsquarters,
B: Common ragweed, P: Pale smartweed

TABLE 1

| Examined Compound | Dosage (g/ha) | crop phytotoxicity | | Herbicidal activity | | |
|---|---|---|---|---|---|---|
| | | T | D | S | B | P |
| Cinidon-ethyl | 10 | 2 | 3 | 2 | 4 | 1 |
| bentazone | 280 | 0 | 0 | 2 | 3 | 4 |
| Cinidon-ethyl + bentazone | 10 + 280 | 2 | 3 | 8 | 9 | 8 |

Effect of the invention

A wide variety of weeds in corn fields, soybean fields, wheat fields, barley fields, oats fields, rye fields, rice fields, paddy fields or the like, can be controlled with selectivity by using the present inventive composition.

What is claimed is:

1. A synergistic herbicidal composition comprising (i) 3-isopropyl-1H-2,1,3-benzothiadiazin-4(3H)-one 2,2-dioxide, and (ii) ethyl 2-chloro-3-[2-chloro-5-(1,3-dioxo-4,5,6,7-tetrahydroisoindolin-2-yl)phenyl]acrylate as active ingredients.

2. The herbicidal composition according to claim 1, wherein the weight ratio of component (i) to component (ii) in said composition is from about 4:1 to 400:1.

3. A method for controlling weeds, which comprises applying a synergistically herbicidally effective amount of (i) 3-isopropyl-1H-2,1,3-benzothiadiazin-4(3H)-one 2,2-dioxide, and (ii) ethyl 2-chloro-3-[2-chloro-5-(1,3-dioxo-4,5,6,7-tetrahydroisoindolin-2-yl)phenyl]acrylate to said weeds.

4. The method for controlling weeds according to claim 3, wherein the weight ratio of component (i) to component (ii) being applied to said weeds is from about 4:1 to 400:1.

5. The method for controlling weeds according to claim 3 or 4, a total amount of components (i) and (ii) being applied to said weeds is from 50 to 5,000 g per hectare.

6. The method according to claim 3, wherein the weeds are those growing in a corn field.

7. The method according to claim 3, wherein the weeds are those growing in a soybean field.

8. The method according to claim 4, wherein the weeds are those growing in a corn field.

9. The method according to claim 5, wherein the weeds are those growing in a corn field.

10. The method according to claim 4, wherein the weeds are those growing in a soybean field.

11. The method according to claim 5, wherein the weeds are those growing in a soybean field.

12. The herbicidal composition according to claim 1, wherein the weight ratio of component (i) to component (ii) in said composition is from about 4:1 to 40:1.

13. The method for controlling weeds according to claim 3, wherein weight ratio of component (i) to component (ii) in said composition is from about 4:1 to 40:1.

* * * * *